United States Patent [19]
Sinderby et al.

[11] Patent Number: 5,820,560
[45] Date of Patent: Oct. 13, 1998

[54] INSPIRATORY PROPORTIONAL PRESSURE ASSIST VENTILATION CONTROLLED BY A DIAPHRAGM ELECTROMYOGRAPHIC SIGNAL

[75] Inventors: Christer Sinderby, Montréal; Alejandro Grassino, Westmount, both of Canada; Sven Friberg; Lars Lindstrom, both of Molndal, Sweden

[73] Assignee: Universite de Montreal

[21] Appl. No.: 848,295

[22] Filed: Apr. 29, 1997

Related U.S. Application Data

[63] Continuation-in-part of Ser. No. 414,494, Mar. 31, 1995, Pat. No. 5,671,752.

[51] Int. Cl.$^6$ .............................................. A61B 5/04
[52] U.S. Cl. ............................................ 600/546; 600/593
[58] Field of Search ..................................... 600/587, 593, 600/546, 547

[56] References Cited

U.S. PATENT DOCUMENTS

| | | | |
|---|---|---|---|
| 4,213,467 | 7/1980 | Stulen et al. .............................. | 128/733 |
| 4,248,240 | 2/1981 | van Eykern . | |
| 5,107,831 | 4/1992 | Halpern et al. ..................... | 128/204.26 |
| 5,212,476 | 5/1993 | Maloney .............................. | 340/825.19 |
| 5,239,995 | 8/1993 | Estes et al. ......................... | 128/204.23 |
| 5,303,700 | 4/1994 | Weismann et al. ................. | 128/204.23 |
| 5,349,963 | 9/1994 | Eskelinen .............................. | 128/733 |
| 5,353,788 | 10/1994 | Miles . | |
| 5,513,631 | 5/1996 | McWilliams ....................... | 128/204.23 |
| 5,520,192 | 5/1996 | Kitney et al. . | |
| 5,671,752 | 9/1997 | Sinderby et al. . | |

FOREIGN PATENT DOCUMENTS

| | | |
|---|---|---|
| 1333036 | 11/1994 | Canada . |
| 2038971 | 6/1996 | Canada . |

OTHER PUBLICATIONS

L.A. Geddes, "Intraoesophageal monitoring of electrocardiogram and respiration in anaesthetised animals", Jan. 1984.

Edward P. Mueller et al., "On–Line Subtraction of the Cardiac Activity from the Esophageal Electromyogram of the Diaphragm", Apr. 1968.

"The Role of the Human Diaphragm Configuration on the EMG Centre Frequency" PP Ruiz–Neto et al ALA/ATS International Conference, May 16–19, 1993—Abstract Form.

(List continued on next page.)

*Primary Examiner*—Max Hindenburg
*Assistant Examiner*—Pamela L. Wingood
*Attorney, Agent, or Firm*—Merek & Voorhees

[57] ABSTRACT

To control a lung ventilator comprising an inspiratory implement to be worn by the patient, an air supply system for supplying air to the inspiratory implement, and a control unit for controlling the air supply system, electromyographic signals produced by the patient's diaphragm are detected by an array of electrodes passing through the center of the patient's diaphragm depolarizing region. The position of the center of the patient's diaphragm depolarizing region is determined through detection of a reversal of polarity of the electromyographic component of the electrode-detected electromyographic signals. First and second electromyographic signals detected by the electrodes of the array on opposite sides of the patient's diaphragm depolarizing region are subtracted from each other, this subtraction cancelling the noise components of the first and second electromyographic signals but adding the respective electromyographic components of these first and second signals together to produce an electromyographic signal having an improved signal-to-noise ratio, having a reduced electrode-position-induced filter effect, and being representative of a demand to inspire from the patient's brain. The electromyographic signal of improved signal-to-noise ratio is finally supplied as input signal to the control unit of the lung ventilator for controlling the air supply system and therefore the inspiration assist in relation to the electromyographic signal of improved signal-to-noise ratio and of reduced electrode-position-induced filter effect, and therefore in relation to the demand to inspire from the patient's brain.

21 Claims, 8 Drawing Sheets

OTHER PUBLICATIONS

"The Role of Diaphragmatic Recruitment in EMG Signal Analysis", J. Weinberg et al. ALA/ATS International Conference, May 16–19, 1993—Abstract Form.

"Automatic EMG Selection for Muscle Fatigue Diagnosis" C. Sinderby et al. ALA/ATS International Conference, May 16–19, 1993—Abstract Form.

"Effect of Esophageal Electrode Distance from the Diaphragm on EMG Center Frequency" J. Beck et al. ALA/ATS International Conference, May 13–19, 1993—Abstract Form.

"The Influence of Innervation Zones on Esophageal Recordings of Diaphragmatic EMG" J. Beck et al. ALA/ATS International Conference, May 22–25, 1994—Abstract Form.

"Effects of Chest Wall Configuration on Esophageal Recordings of Diaphragm EMG" J. Beck et al. ALA/ATS International Conference, May 22–25, 1994—Abstract Form.

"Effects of Chest Wall Configuration and Electrode Positioning on Human Diaphragmatic EMG" J. Beck, A thesis, McGill Univesity, Oct. 1994, pp. i–viii and 1–150.

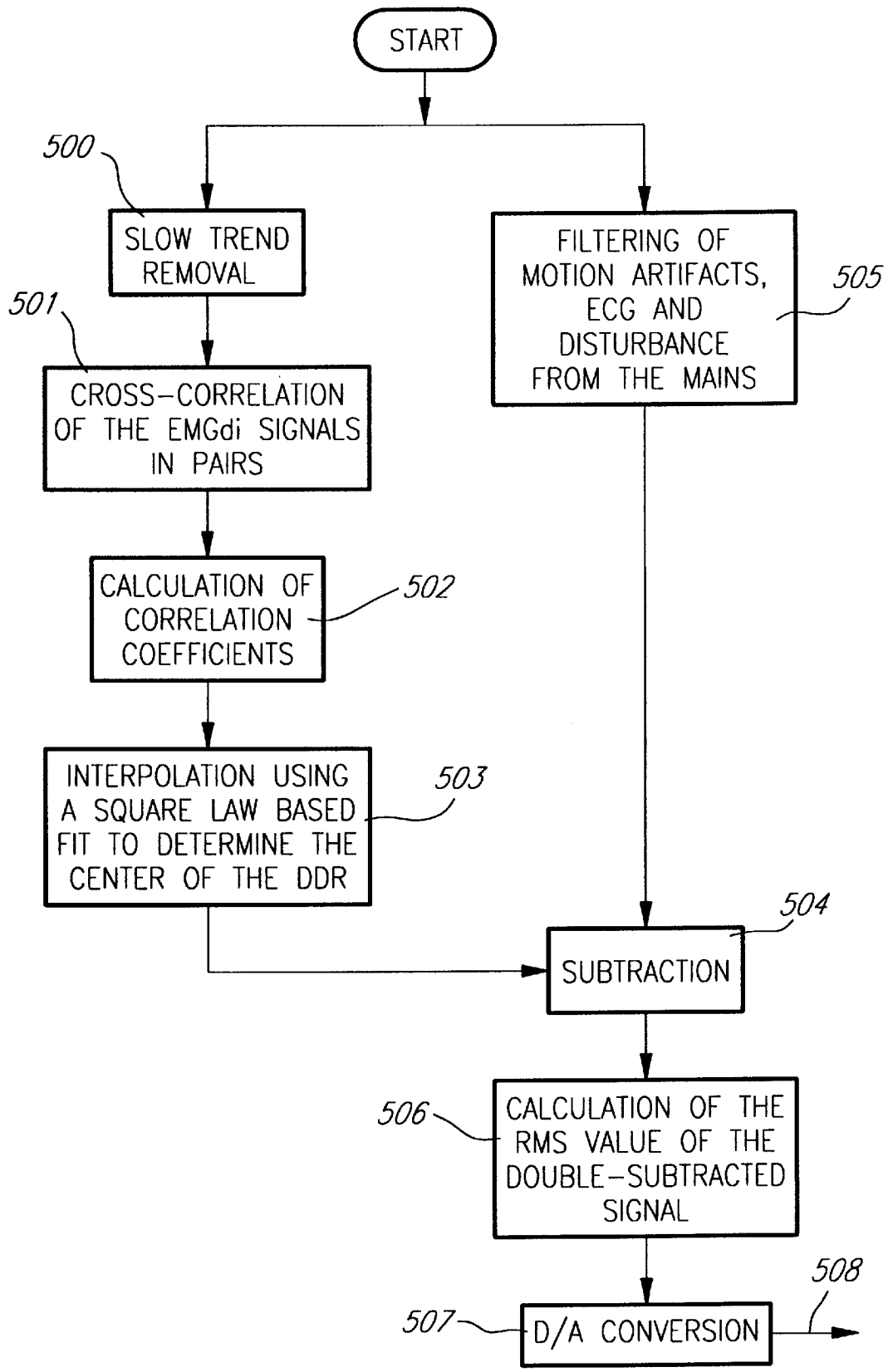

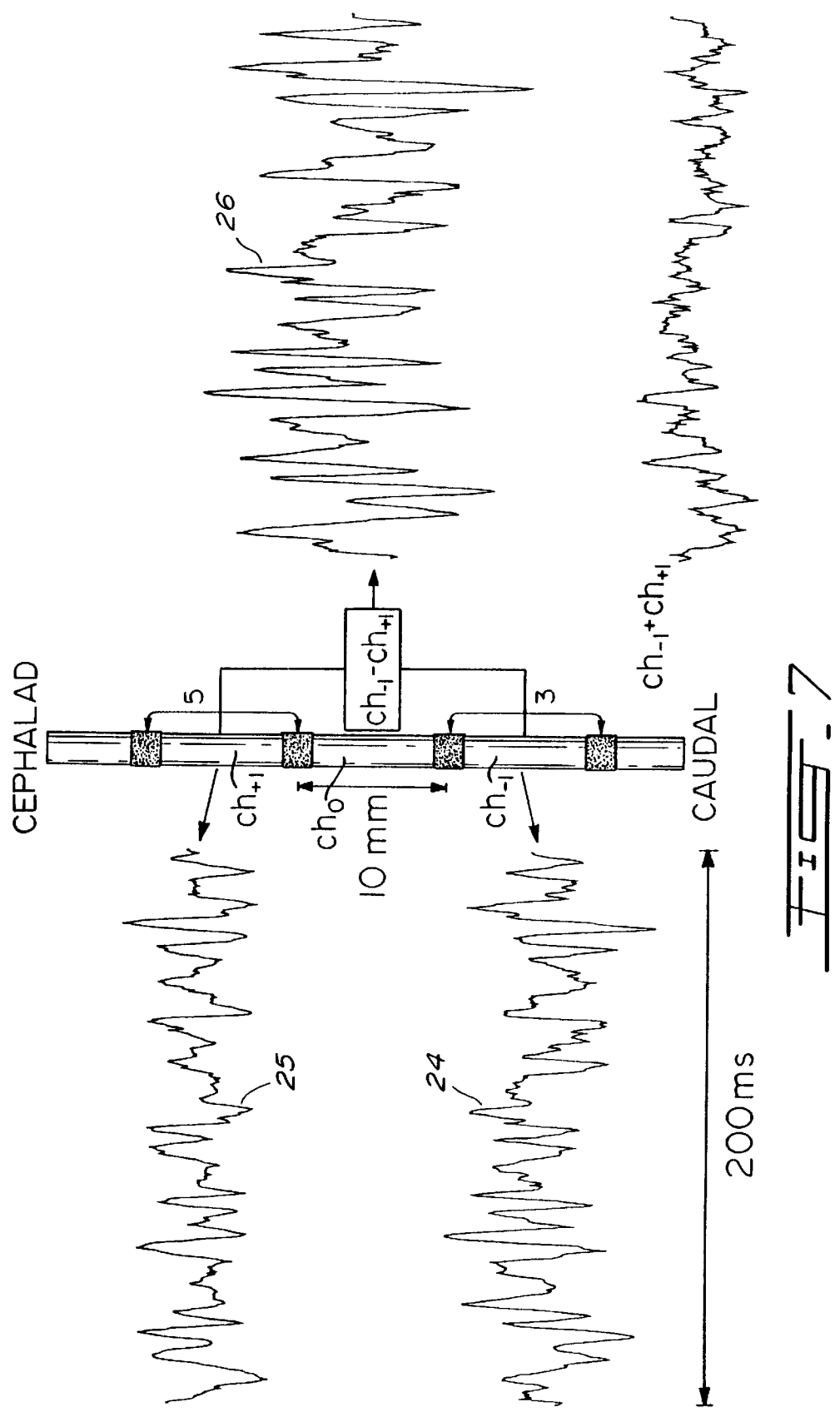

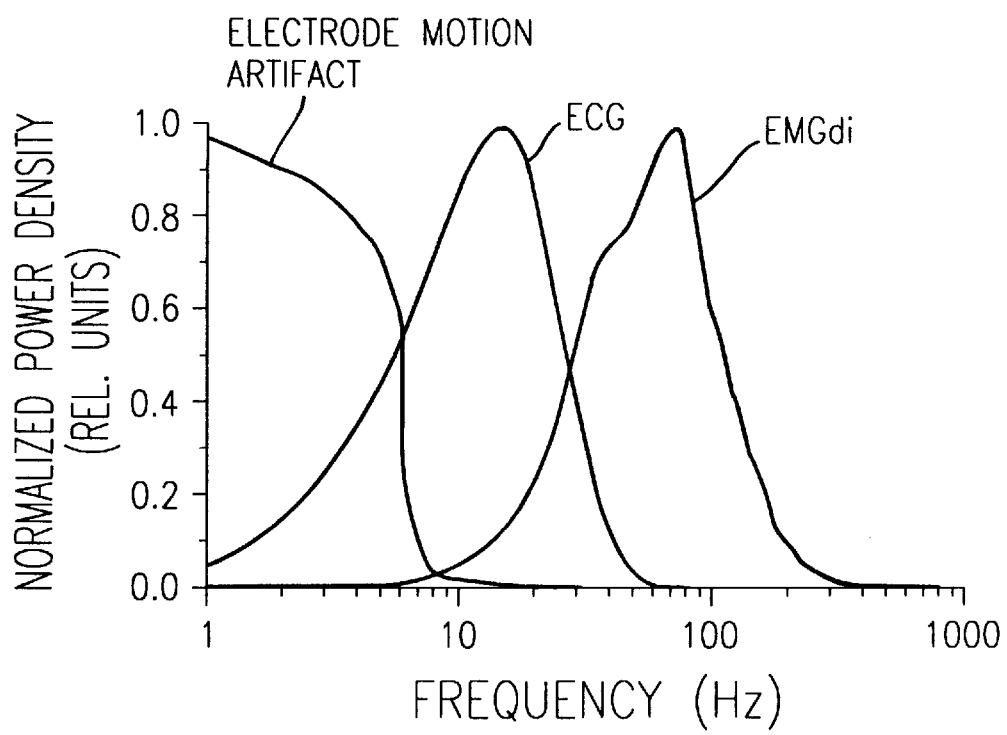
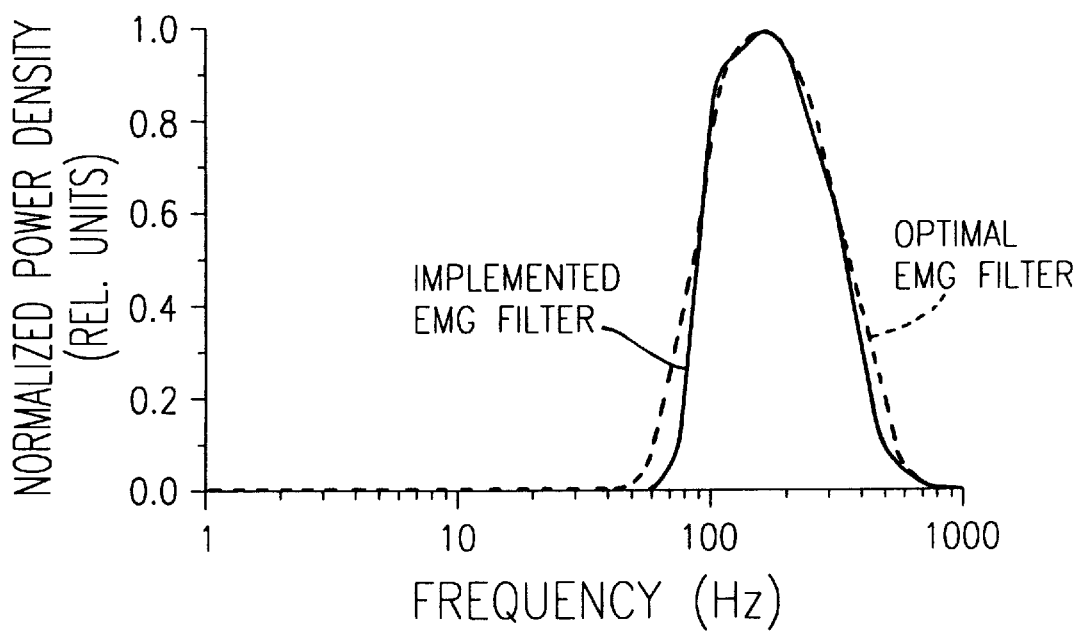

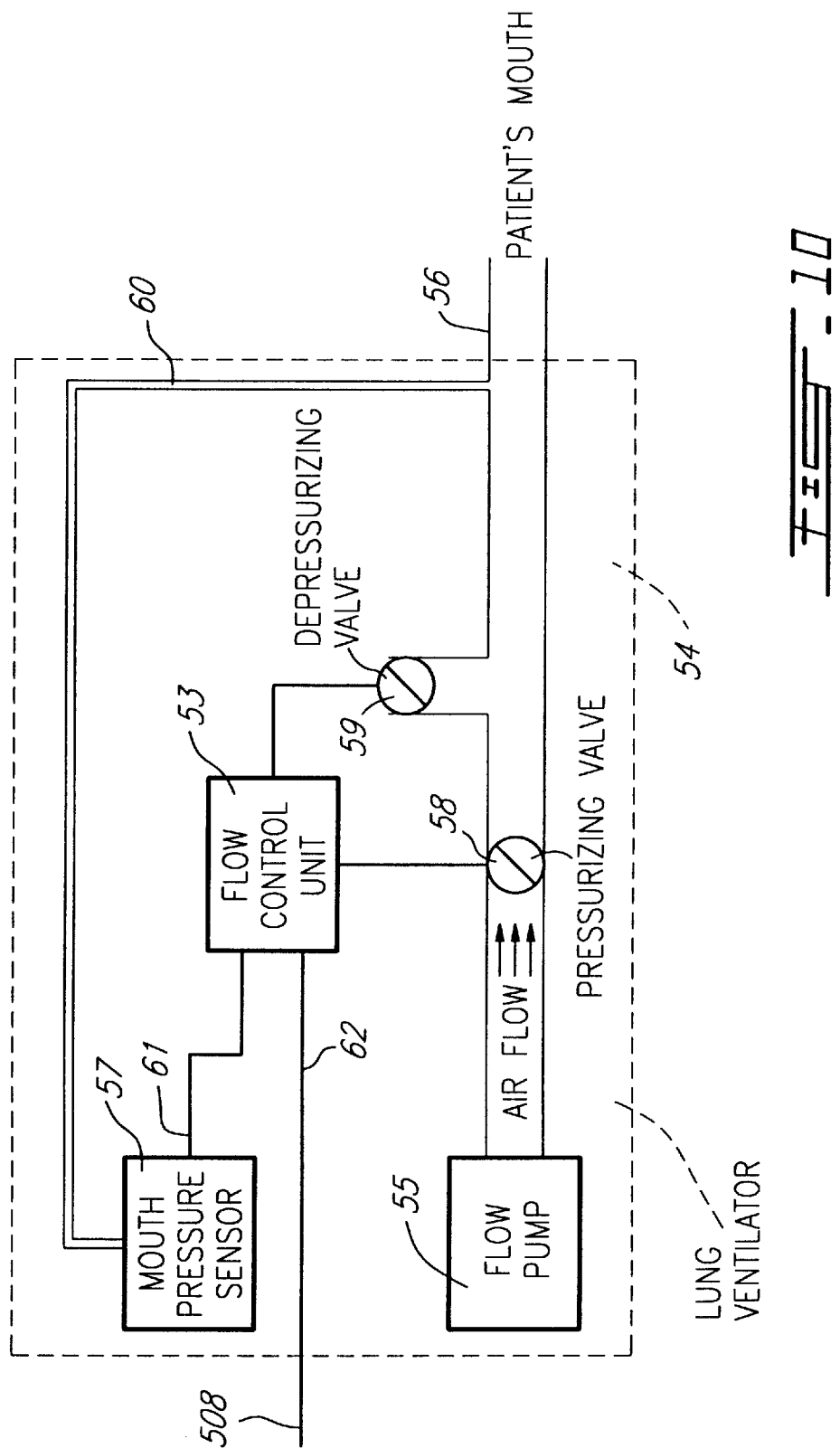

INSPIRATORY PROPORTIONAL PRESSURE ASSIST VENTILATION CONTROLLED BY A DIAPHRAGM ELECTROMYOGRAPHIC SIGNAL

CROSS-REFERENCE TO RELATED APPLICATION

This is a Continuation-in-part of U.S. patent application Ser. No. 08/414,494 filed by Christer SINDERBY et al on Mar. 31, 1995 for an invention entitled "DIAPHRAGM ELECTROMYOGRAPHY ANALYSIS METHOD AND SYSTEM", now U.S. Pat. No. 5,671,752.

BACKGROUND OF THE INVENTION

1. Field of the invention:

The present invention relates to the control of a lung ventilator by means of an electromyographic (EMG) signal produced by detecting EMGdi signals of reverse polarities on opposite sides of the center of the diaphragm depolarizing region and by subtracting these EMGdi signals to improve the signal-to-noise ratio and to reduce an electrode-position-induced filter effect.

2. Brief description of the prior art:

The physiological mechanisms which generate myoelectrical activity when a muscle contracts have been known and understood for a long time. In particular, how to record signals from the muscles is one of the most extensively, theoretically described topics in physiology. Although the theoretical understanding is impressive, the bio-physiological application of these theories is, in practice, still deficient. As an example, no standardized analysis procedure has been developed for recording signals produced by activation of several, different motor units, the so called interference wave pattern. The interference wave pattern signal (EMG signal) contains an immense quantity of bio-physiological information about the given neuro-muscular function. However, as this EMG signal is very low in amplitude, it is sensitive to numerous artifacts. The influence of these artifacts varies in relation to the configuration of recording electrodes, the digitizing rate of the signal, and the type of recording technique.

Prior art analysis of interference wave pattern signals usually comprises a time consuming, tedious manual determination of the quality of the signal through visual inspection of this signal in the time domain. This determination is performed by a "subjective" investigator. Most of the prior art references describe how to calculate comparison estimates, but present very few comments on the signal quality. It is therefore not surprising to find that, in this technical field, independent studies evaluating the same questions have lead to different or even contradictory results.

Also in the prior art, the patient's inspiratory flow and volume has been used to control inspiratory proportional pressure assist ventilation. Proper adjustment of the relative contribution of flow and volume support during the inspiration requires knowledge of the elastic and viscous properties of the patient's respiratory system. Since the elastic and viscous properties may change, these measurements must be repeated at regular intervals. Correct and repeated measurements of elastance and resistance are difficult to set up in an intensive care unit. Moreover, in the presence of intrinsic positive end-expiratory pressure, the flow-volume controlled proportional assist ventilation may fail to trigger during whole breaths, and will definitively fail to trigger during at least the initial part of the inspiration which precedes the onset of flow; this period can last up to 300 ms in the case of a patient suffering from obstructive pulmonary disease. Finally leakage in the system will influence and may disturb the performance of the flow controlled proportional assist ventilation.

OBJECTS OF THE INVENTION

An object of the present invention is therefore to overcome the above described drawbacks of the prior art.

Another object of the present invention is to provide a method and a device capable of adjusting the degree of inspiratory assist in relation to the real need of the patient, i.e. only to compensate for the degree of incapacity of the patient.

A further object of the present invention is to provide a method and a device for controlling inspiratory proportional pressure assist ventilation which requires no knowledge of the elastic and viscous properties of the patient's respiratory system, is not influenced by intrinsic positive end-expiratory pressure, and is not influence by air leakage of the lung ventilator unless the leakage exceeds the pumping capacity of the ventilator.

SUMMARY OF THE INVENTION

More specifically, in accordance with the present invention, there is provided a method of controlling a lung ventilator in view of assisting inspiration of a patient, the lung ventilator comprising an inspiratory implement to be worn by the patient, an air supply system for supplying air to the inspiratory implement in order to assist patient's inspiration, and a control unit for controlling the air supply system in relation to an input signal. This method comprises the step of detecting electromyographic signals produced by the patient's diaphragm by means of an array of electrodes passing through the center of the patient's diaphragm depolarizing region, each electrode-detected electromyographic signal comprising an electromyographic component and a noise component. The position of the center of the patient's diaphragm depolarizing region is determined by detecting a reversal of polarity of the electromyographic component of the electrode-detected electromyographic signals. A first electromyographic signal detected by the electrodes of the array on a first side of the center of the patient's diaphragm depolarizing region is subtracted from a second electromyographic signal detected by the electrodes of the array on a second side, opposite to the first side, of the center of the patient's diaphragm depolarizing region. The first electrode-detected electromyographic signal has an electromyographic component of a first polarity, the second electrode-detected electromyographic signal has an electromyographic component of a second polarity opposite to the first polarity, the subtraction subtracts the noise components of the first and second electrode-detected electromyographic signals from each other but adds the respective electromyographic components of the first and second electrode-detected electromyographic signals together to produce an electromyographic signal of improved signal-to-noise ratio representative of a demand to inspire from the patient's brain. The electromyographic signal of improved signal-to-noise ratio is supplied as input signal to the control unit of the lung ventilator for controlling the air supply system and therefore the inspiration assist in relation to the electromyographic signal of improved signal-to-noise ratio.

By using an electromyographic signal of improved signal-to-noise ratio representative of a demand to inspire from the patient's brain, the degree of inspiratory assist can be adjusted in relation to the real need of the patient, i.e. only to compensate for the degree of incapacity of the patient. The patient still contributes to inspiration as a function of his capacity to prevent the lung ventilator to further reduce the patient's inability to breathe.

The present invention also relates to a device for controlling a lung ventilator in view of assisting inspiration of a patient, the lung ventilator comprising an inspiratory implement to be worn by the patient, an air supply system for supplying air to the inspiratory implement in order to assist patient's inspiration, and a control unit for controlling the air supply system in relation to an input signal. The device of the invention comprises:

an array of electrodes for detecting electromyographic signals produced by the patient's diaphragm, the array of electrodes passing through the center of the patient's diaphragm depolarizing region, and each electrode-detected electromyographic signal comprising an electromyographic component and a noise component;

means for determining the position of the center of the patient's diaphragm depolarizing region by detecting a reversal of polarity of the electromyographic component of the electrode-detected electromyographic signals;

means for subtracting a first electromyographic signal detected by the electrodes of the array on a first side of the center of the patient's diaphragm depolarizing region, from a second electromyographic signal detected by the electrodes of the array on a second side, opposite to the first side, of the center of the patient's diaphragm depolarizing region, wherein (a) the first electrode-detected electromyographic signal has an electromyographic component of a first polarity, (b) the second electrode-detected electromyographic signal has an electromyographic component of a second polarity opposite to the first polarity, (c) the subtraction subtracts the noise components of the first and second electrode-detected electromyographic signals from each other but adds the respective electromyographic components of the first and second electrode-detected electromyographic signals together to produce an electromyographic signal of improved signal-to-noise ratio representative of a demand to inspire from the patient's brain; and means for supplying the electromyographic signal of improved signal-to-noise ratio as input signal to the control unit of the lung ventilator for controlling the air supply system and therefore the inspiration assist in relation to the electromyographic signal of improved signal-to-noise ratio.

Preferably, the array of electrodes is a linear array of electrodes and defines a plurality of pairs of successive electrodes, the center of the patient's diaphragm depolarizing region is located between the electrodes of a given one of the pairs of successive electrodes, the first electromyographic signal is detected through the pair of successive electrodes adjacent to the given pair on one side of that given pair, and the second electromyographic signal is detected through the pair of successive electrodes adjacent to the given pair on the other side of that pair.

The position of the center of the patient's diaphragm depolarizing region may be determined through cross-correlation of the electrode-detected electromyographic signals. Prior to the cross-correlation, a slow trend is advantageously removed from the electrode-detected electromyographic signals.

The subtraction may be carried out in the time domain or in the frequency domain.

According to other preferred embodiments:

a RMS value of the electromyographic signal of improved signal-to-noise ratio is calculated and supplied as input signal to the control unit of the lung ventilator;

motion artifacts, an ECG component, and a disturbance from electrical mains are filtered from the electrode-detected electromyographic signals prior to the subtraction of the first electrode-detected electromyographic signal from the second electrode-detected electromyographic signal;

the patient's respiratory pressure is detected and a pressure representative signal is produced, the pressure representative signal is supplied to the control unit of the lung ventilator, and the control unit controls the air supply system in relation to a difference between the pressure representative signal and the electromyographic signal of improved signal-to-noise ratio; and the array of electrodes is a linear array of electrodes mounted on a free end section of a catheter.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 5 is a flow chart showing a method for conducting double subtraction technique of the EMGdi signals;

FIG. 7 is a schematic diagram illustrating in the time domain a double subtraction technique for improving the signal-to-noise ratioratio and to reduce an electrode-position-induced filter effect;

FIG. 8a is a graph showing the power density spectrum of electrode motion artifacts, the power density spectrum of ECG, and the power density spectrum of EMGdi signals;

FIG.8b is a graph showing an example of transfer function for a filter to be used for filtering out the electrode motion artifacts, ECG, and the 50 or 60 Hz disturbance from electrical mains;

FIG. 10 is a schematic block diagram of a lung ventilator showing control of inspiratory proportional pressure assist ventilation by means of an EMG signal obtained with the above mentioned double subtraction technique.

DETAILED DESCRIPTION OF THE PREFERRED EMBODIMENT

To measure EMG activity of the diaphragm 11 (EMGdi) of a human patient 14, an array of electrodes such as 12

Figure 1:
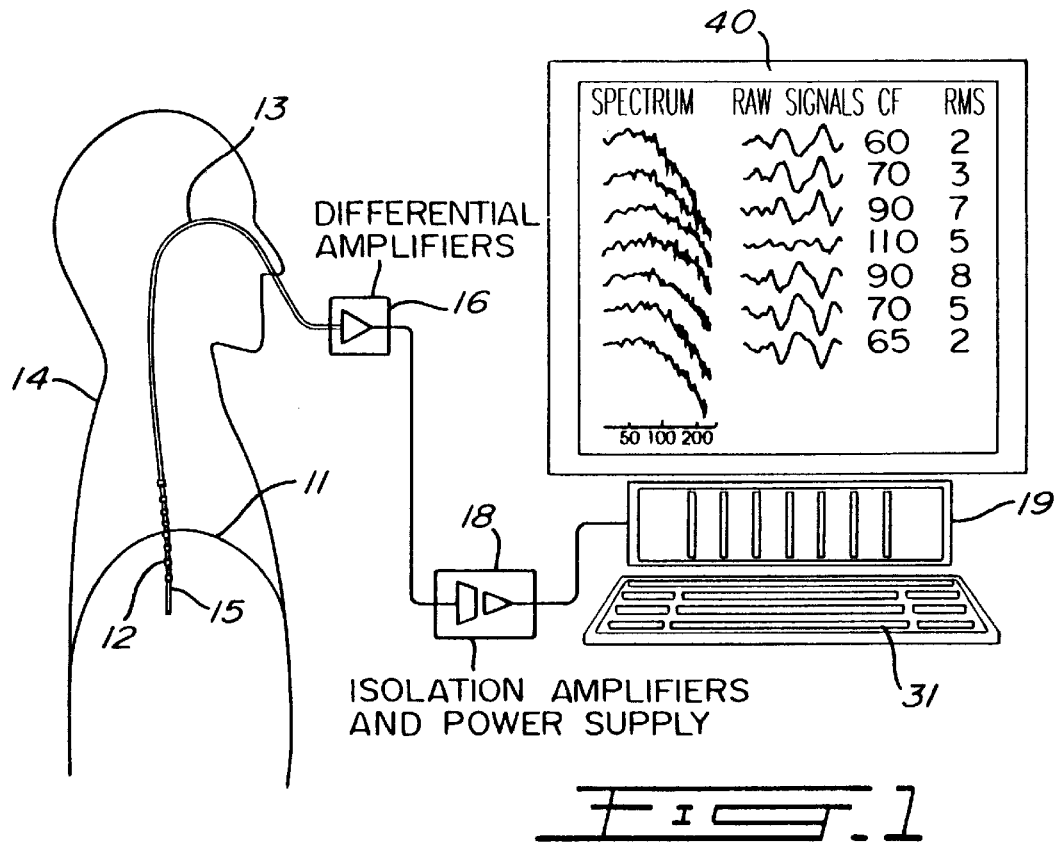
FIG. 1 is a schematic representation of a set-up of an EMG analysis system.
Figure 2:
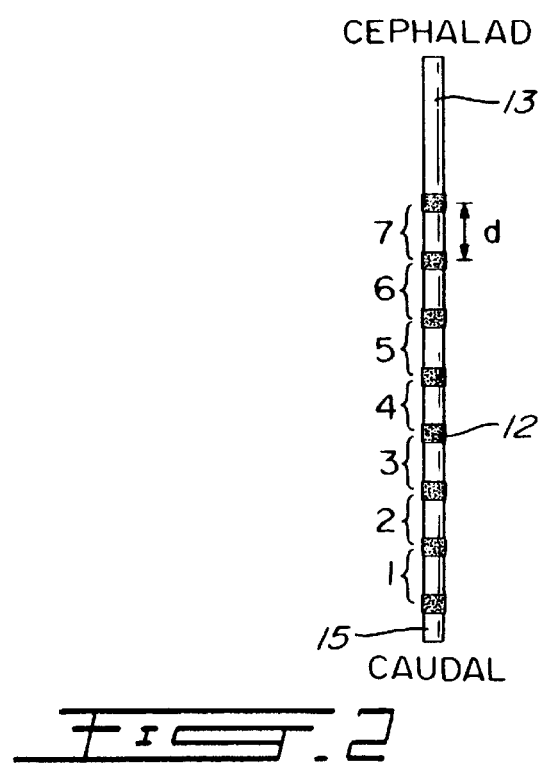
FIG. 2 is a section of oesophageal catheter on which an array of electrodes of the EMG analysis system of FIG. 1 is mounted.

(FIGS. 1 and 2) are mounted on the free end section 15 of an oesophageal catheter 13, with a constant inter-electrode distance d (FIG. 2). As shown in FIG. 1, the catheter 13 is introduced into the patient's oesophagus through one nostril or the mouth until the array of electrodes 12 are situated at the level of the gastroesophageal junction. The diaphragm 11 and/or the oesophagus slightly move during breathing of the patient 14 whereby the array of electrodes 12 also slightly moves about the diaphragm 11. As will be explained in the following description, automatic compensation for this displacement is provided.

To mount an electrode 12 on the free end section 15 of the catheter 13, stainless steel wire (not shown) may be wound around the catheter 13. The wound stainless steel wire presents a rough surface smoothed out by solder, which in turn is electroplated with nickel, copper and then gold or silver. Of course, other constructions of electrodes can be implemented.

Electric wires (not shown) interconnect each pair of successive electrodes such as 1–7 (FIG. 2) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EMGdi signals collected by the various pairs 1–7 of electrodes 12 are shielded to reduce the influence of external noise, in particular disturbance from the 50 or 60 Hz current and voltage of the electrical mains.

The group of differential amplifiers 16 amplifies (first subtraction step of the double subtraction technique) and band-pass filters each EMGdi signal. This first subtraction step may also be carried out in the personnal computer 19 when the amplifiers 16 are single-ended or equivalently designed amplifiers (monopolar readings).

Figure 3:
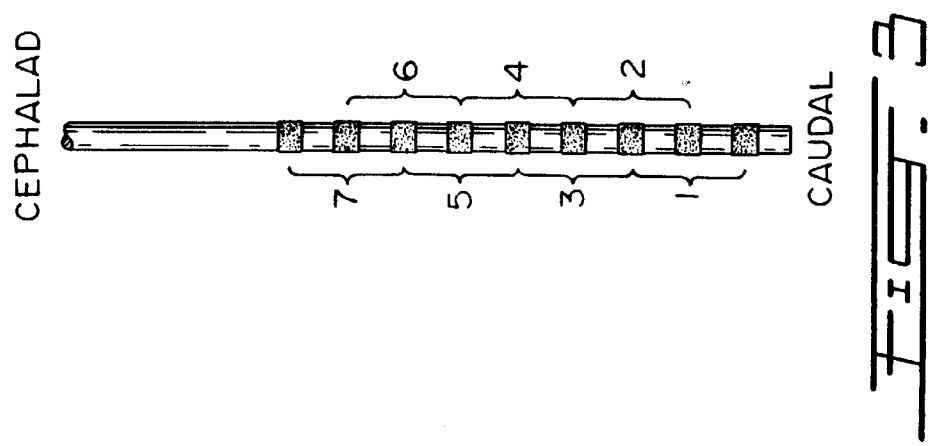
FIG. 3 illustrates a section of oesophageal catheter on which a second embodiment of the array of electrodes is mounted.

In the example illustrated in FIGS. 1 and 2, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that EMG activity of the diaphragm (EMGdi) can be measured accurately with an oesophageal catheter 13 provided on the free end section 15 thereof with an array of eight electrodes 12, a different number and/or configuration of pairs of electrodes 12 can be contemplated depending on the patient's anatomy and movement of the diaphragm. Also, the pairs 1–7 do not need to be pairs of successive electrodes; FIG. 3 illustrates an array of nine electrodes to form seven overlapping pairs of electrodes 1–7.

A major problem in recording EMGdi signals is to maintain the noise level as low and as constant as possible. Since the electric wires transmitting the EMGdi signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is preferably made as small as possible (miniaturized) and is positioned in close proximity to the patient's nose to decrease as much as possible the distance between the electrodes 12 and the amplifiers 16.

The amplified EMGdi signals are supplied to a personal computer 19 through respective isolation amplifiers of a unit 18. Unit 18 supplies electric power to the various electronic components of the differential and isolation amplifiers while ensuring adequate isolation of the patient's body from such power supply. The unit 18 also incorporates bandpass filters included in the respective EMGdi signal channels to eliminate the effects of aliasing. The EMGdi signals are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 31.

It is believed to be within the capacity of those of ordinary skill in the art to construct suitable differential amplifiers 16 and an adequate isolation amplifiers and power supply unit 18. Accordingly, the amplifiers 16 and the unit 18 will not be further described in the present specification.

Figure 4:
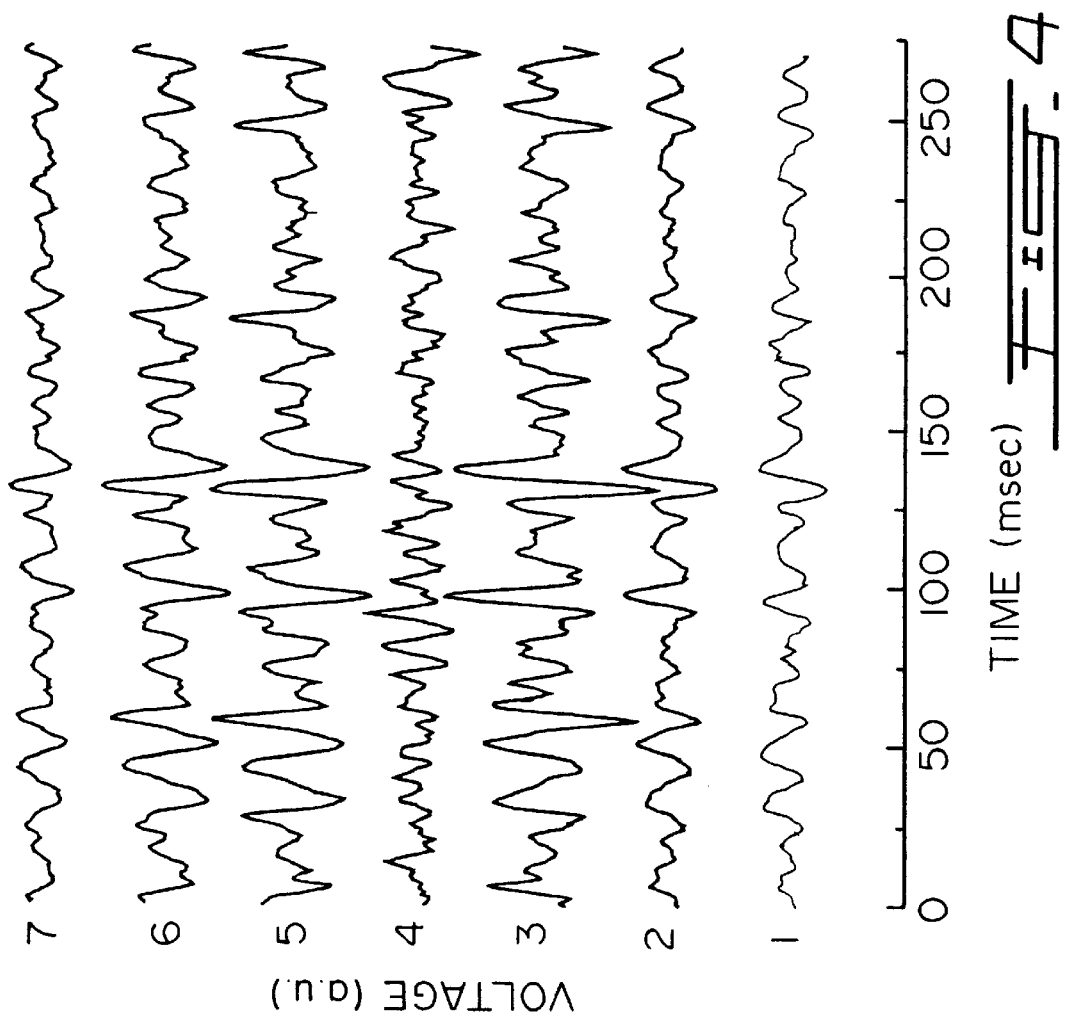
FIG. 4 is a graph showing a set of EMGdi signals of the diaphragm detected by pairs of successive electrodes of the array of FIG. 2.

An example of the seven EMGdi signals collected by the pairs 1–7 of successive electrodes 12 (FIGS. 1 and 2) and supplied to the computer 19 is illustrated in FIG. 4.

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array.

The portion of the crural diaphragm 11 which forms the muscular tunnel through which the oesophageal catheter 13 is passed is referred to the "diaphragm depolarizing region" (DDR). The thickness of the DDR is 20–30 mm. It can be assumed that, within the DDR, the distribution of active muscle fibers has a center from which the majority of the EMGdi signals originate, i.e. the "diaphragm depolarizing region center" (DDR center). Therefore, EMGdi signals detected on opposite sides of the DDR center will be reversed in polarity with no phase shift; in other words, EMGdi signals obtained along the electrode array are reversing in polarity at the DDR center.

Moving centrally from the boundaries of the DDR, EMGdi power spectrums progressively attenuate and enhance in frequency. Reversal of signal polarity on either side of the electrode pair 4 with the most attenuated power spectrum confirms the position from which the EMGdi signals originate, the DDR center.

Referring to FIG. 5, the first task of the computer 19 is to determine the center of the DDR. The center of the DDR is repeatedly determined at predetermined time intervals.

For that purpose, slow trend is first removed from each EMGdi signal (step 500). To carry out such trend removal, the processing conducted by the computer 19 on each EMGdi signal is equivalent to high-pass filtering each EMGdi signal at a transition frequency of about 20 Hz. In particular, step 500 will remove the direct current component of the EMGdi signals to enable the computer 19 to evaluate the polarities of the EMGdi signals relative to each other.

In step 501, the EMGdi signals are cross-correlated in pairs. As well known to those of ordinary skill in the art, cross-correlation is a statistical determination of the phase relationship between two signals and essentially calculates the similarity between two signals in terms of a correlation coefficient r (step 502). A negative correlation coefficient r indicates that the cross-correlated signals are of opposite polarities.

Figure 6:
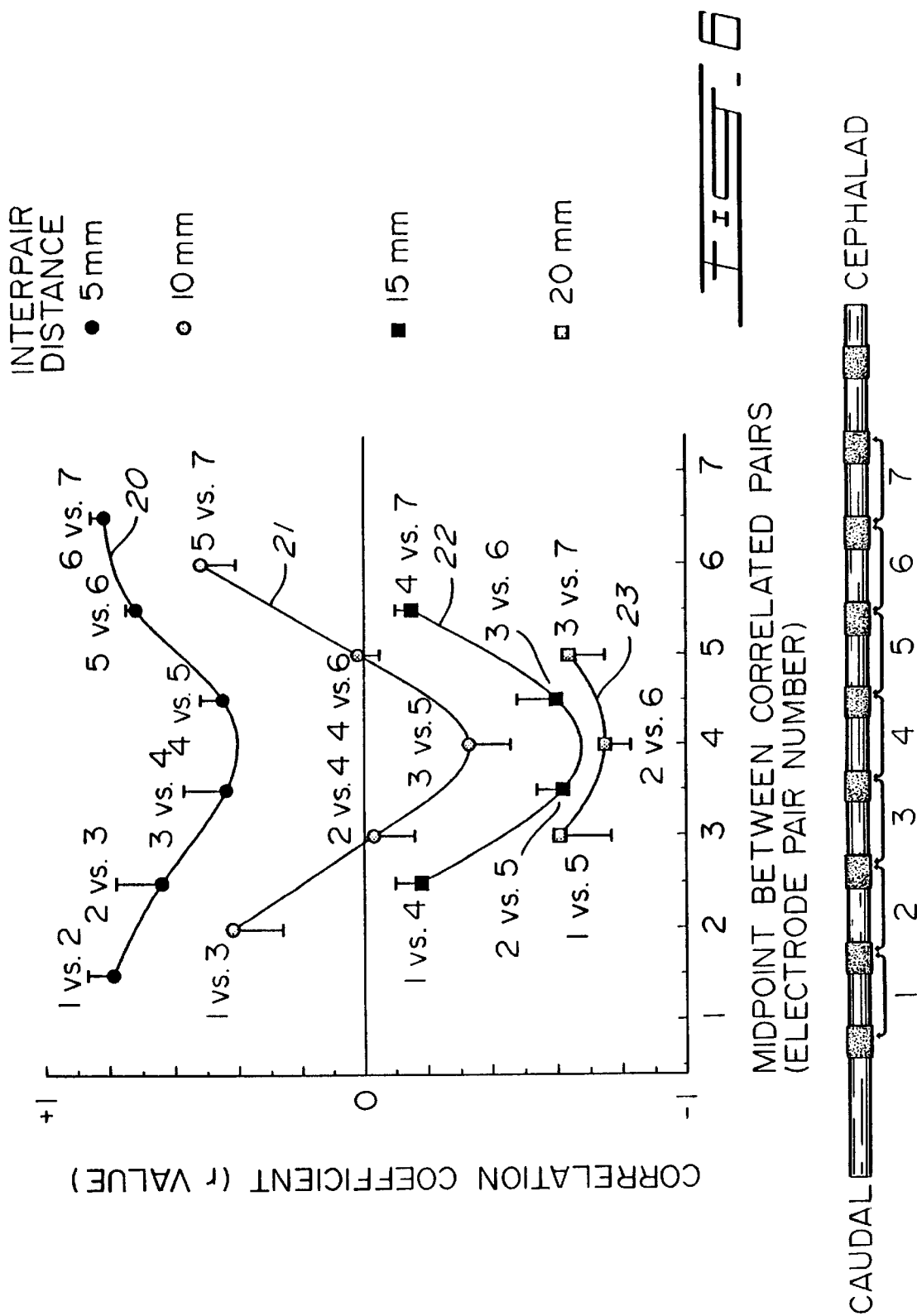
FIG. 6 is a graph showing the distribution of correlation coefficients calculated for determining the position of the center of the depolarizing region of the diaphragm along the array of electrodes of FIG. 2.

FIG. 6 shows curves of the value of the correlation coefficient r versus the midpoint between the pairs of electrodes from which the correlated EMGdi signals originate. In this example, the inter-electrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 5 that negative correlation coefficient r are obtained when EMGdi signals from respective electrode pairs situated on opposite sides of the electrode pair 4 are cross-correlated. It therefore appears that the change in polarity occur in the region of electrode pair 4, which is confirmed by the curves of FIG. 4. Accordingly, it can be assumed that the center of the DDR is situated substantially midway between the electrodes 12 forming pair 4.

For example, the center of the DDR can be precisely determined by interpolation (step 503 of FIG. 5) using a square law based fit of the three most negative correlation coefficients of curve 21 obtained by successive cross-correlation of the EMGdi signals from each electrode pair to the EMGdi signals from the second next electrode pair. Association of the center of the DDR to a pair of electrodes 12 provides a "reference position" from which to obtain EMGdi signals within the DDR. Such control is essential in overcoming the artifactual influence on the EMGdi power spectrum.

It has been experimentally demonstrated that EMGdi signals recorded in the oesophagus are satisfactory as long as they are obtained from electrode pairs (with an inter-electrode distance situated between 5 and 20 mm) positioned at a distance situated between 5 and 30 mm on the opposite sides of the DDR center (the inter-pair distance being therefore situated between 5 and 30 mm). Although EMGdi signals obtained from these positions offers a clear improvement in acceptance rate, the signal-to-noise ratio during quiet breathing still tends to remain unsatisfactorily low.

For example, in FIG. 4, the EMGdi signals originating from the electrode pairs 3 and 5 situated respectively 10 mm below and 10 mm above the DDR are strongly inversely correlated at zero time delay. In contrast to the inversely correlated EMGdi signals, the noise components for electrode pairs 3 and 5 are likely to be positively correlated. Hence, as illustrated in FIG. 7, subtraction of the EMGdi signals 24 and 25 from electrode pairs 3 and 5 will result into an addition of the corresponding EMGdi signals (signal 26 of FIG. 6) and into a subtraction, that is an elimination of the common noise components. This technique will be referred to as "the double subtraction technique" (step 504 of FIG. 5).

Subtraction step 504 (second subtraction step of the double subtraction technique) can be carried out either in the time domain, or after conversion of signals 24 and 25 in the frequency domain. Double subtraction technique can be performed by subtracting other combinations of signals, for example by subtracting the EMGdi signal from electrode pair 2 from the EMGdi signal from electrode pair 5 (FIG. 4), by subtracting signal from electrode pair 6 from the signal from electrode pair 3 and by adding these differences, etc. What is important is to subtract two signals of opposite polarities obtained in the vicinity of the muscle.

The double subtraction technique is carried out in step 504 on the pair of EMGdi signals (for example the signals from electrode pairs 3 and 5 shown in FIG. 4) identified in step 503, after appropriate filtering of these EMGdi signals in step 505. Filtering step 505 will remove from each EMGdi signal the motion artifacts, the electrocardiogram (ECG) component, and the disturbance from the electrical mains. Motion artifacts are induced by motion of the electrodes. More generally, motion artifacts are defined as a low frequency fluctuation of the EMGdi signals' DC level induced by mechanical alterations of the electrode metal to electrolyte interface i.e. changes in electrode contact area and/or changes in pressure that the tissue exerts on the electrode.

The graph of FIG. 8a shows the power density spectrum of the above defined electrode motion artifacts, the power density spectrum of ECG, and the power density spectrum of EMGdi signals. The graph of FIG. 8b shows an example of transfer function for a filter (the dashed line showing the optimal transfer function, and the solid line the transfer function implemented by the inventors) to be used in step 505 for filtering out the electrode motion artifacts, ECG, and the 50 or 60 Hz disturbance from the electrical mains. Processing of the EMGdi signals by the computer 19 to follow as closely as possible the optimal transfer function of FIG. 8b will conduct adequately filtering step 505.

Referring back to FIG. 5, step 506 calculates the RMS (Root-mean-square) value of the double-subtracted signal produced in step 504. The increase in amplitude obtained with the double subtraction technique is associated with a twofold increase in RMS values. RMS values obtained with the double subtraction technique are closely and linearly related to the original signals. The RMS value can be replaced by any other value representative of the strenght of the double-subtracted signal.

The digital RMS value calculated by the computer 19 in step 506 is finally converted to an on-line analog RMS value (step 507) which is outputted on line 508 in view of controlling a lung ventilator 54 (FIG. 10).

Figure 9:
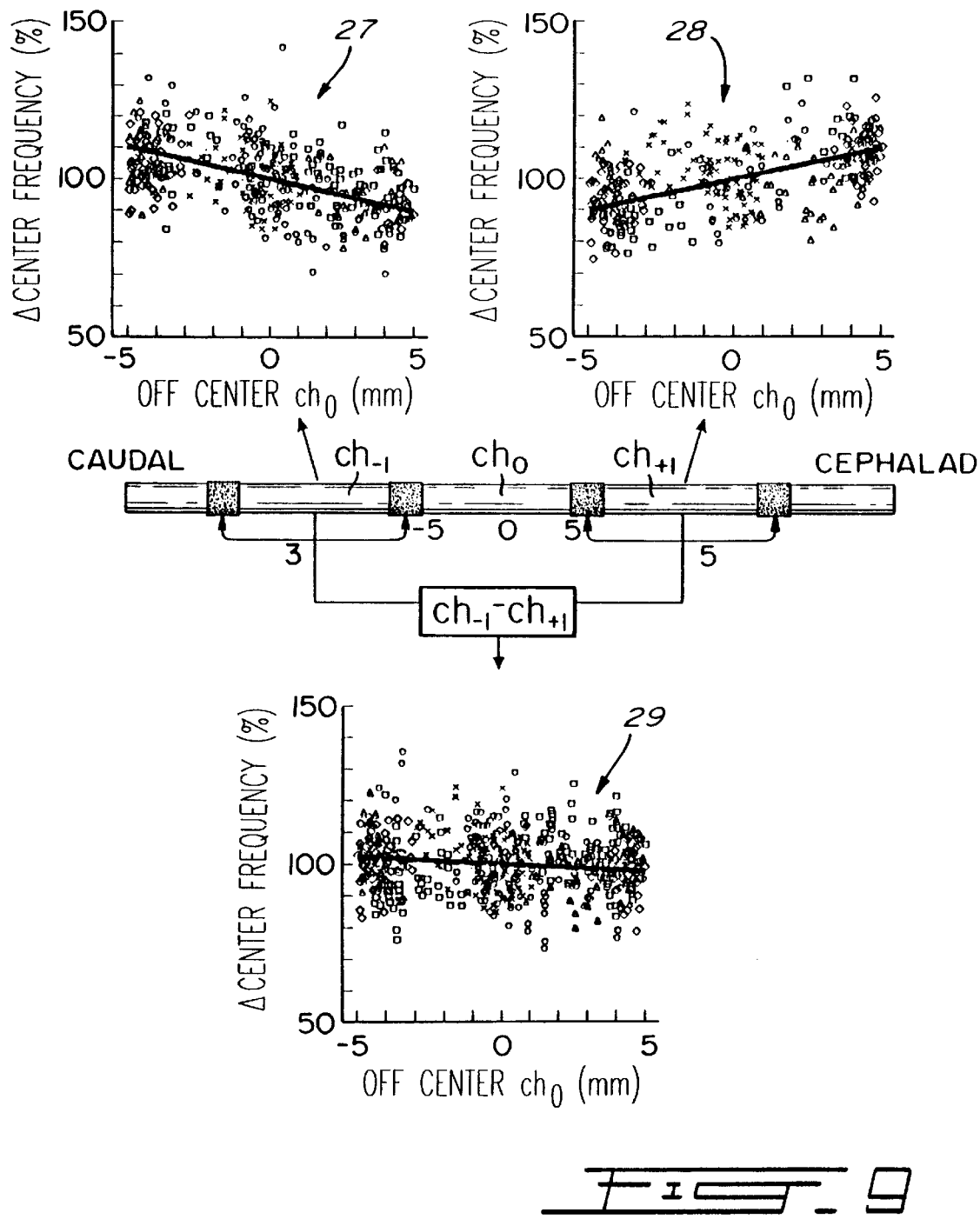
FIG. 9 is schematic diagram illustrating in the frequency domain stabilization by the double subtraction technique of the center frequency upon displacement of the center of the depolarizing region of the diaphragm along the array of electrodes of FIG. 2.

The double subtraction technique compensates for the changes in signal strenght and frequency caused by movement of the diaphragm 11 (FIG. 1) and/or the oesophagus during breathing of the patient 14 causing movement of the array of electrodes 12 with respect to the diaphragm 11. Referring to FIG. 9, off center of the array of electrodes 12 (electrode-position-induced filter effect) causes a variation of center frequency values (see curves 27 and 28) for the EMGdi signals from the electrode pairs 3 and 5. The double subtraction technique eliminates such variation of center frequency values as indicated by curve 29 as well as variation of signal strenght. Therefore, the reciprocal influence of the position of the DDR center on the EMGdi signal frequency content is eliminated by the double subtraction technique.

It has been found that the double subtraction technique may improve the signal-to-noise ratio by more than 2 dB ratio and reduce an electrode-position-induced filter effect. Double subtraction technique is also responsible for a relative increase in acceptance rate by more than 30%.

Cross-talk signals from adjacent muscles are strongly correlated at zero time delay and equal in polarity between all pairs of electrodes 12. Hence, these cross-talk signals appear as a common mode signal for all electrode pairs and therefore, are eliminated by the double subtraction technique.

FIG. 10 illustrates a lung ventilator 54 capable of being controlled by the analog RMS value of the double-subtracted signal produced in step 507 of FIG. 5. Although an air-flow-based pressure ventilator is illustrated as an example in FIG. 10, it should be kept in mind that the analog RMS value of the double subtracted signal can be used for controlling any other lung ventilator.

Ventilator 54 shown in FIG. 10 as an illustrative example only comprises a flow control unit 53, a flow pump 55, a patient's respiratory (inspiratory and expiratory) implement 56 such as a mask, a trachial tube connector, or any other respiratory implement, a pressure sensor 57, a pressurizing valve 58, and a depressurizing valve 59.

The flow pump 55 produces a constant air flow and supply of this air flow to the patient's respiratory accessory 56 is controlled through the pressurizing valve 58. The patient is allowed to breathe out through the respiratory accessory 56 and the depressurizing valve 59. The pressurizing and depressurizing valves 58 and 59 are controlled by the flow control unit 53.

The pressure sensor 57 is connected close to the respiratory implement 56 through a line 60. The pressure sensor 57 produces a corresponding respiratory pressure representative signal 61 supplied to the flow control unit 53. Accordingly, the pressure sensor 57 provides feedback of actual respiratory pressure close to the respiratory implement 56. The flow control unit 53 is also supplied with the analog RMS value 62 of the double-subtracted signal delivered on line 508 by step 507 of FIG. 5.

Those of ordinary skill in the art know that the amplitude of the analog RMS value 62 of the double-subtracted signal delivered on line 508 is a representation of the demand to breathe from the brain.

When the analog RMS value 62 supplied to the flow control unit 53 is higher than the amplitude of the pressure representative signal 61, this indicates that the demand to breath from the brain is higher than the air actually breathed by the patient. Inspiratory assist is then required and the flow control unit 53 will open pressurizing valve 58 to supply air flow from the pump 55 to the patient's respiratory accessory (depressurizing valve 59 being closed) until the amplitude of the pressure representative signal 61 is equal to the analog RMS value 62. The flow control unit 53 will continue to control the position of valve 58 to maintain the amplitude of the pressure representative signal 61 equal to the analog RMS value 62 during all the inspiratory cycle.

During the inspiratory cycle, when the analog RMS value 62 falls slightly below the amplitude of the pressure representative signal 61, depressurizing valve 59 can be opened to correct the situation and maintain the amplitude of the pressure representative signal 61 equal to the analog RMS value 62.

When the analog RMS value 62 drops below a given threshold, this indicates the beginning of an expiratory cycle. Then, the flow control unit 53 closes pressurizing valve 58 and opens depressurizing valve 59 to allow the patient to breath out through the respiratory accessory 56 and the depressurizing valve 59.

In order to obtain correct proportionality between the pressure representative signal 61 and the analog RMS value 62, a gain adjustment is introduced for example in sensor 57 or on the line 508 to adequately control pressure assist to the respiratory implement 56 in function of the analog RMS value 62.

Accordingly, the subject invention presents a major advantage over the prior art. Indeed, the degree of inspiratory assist is adjusted in relation to the real need of the patient. In other words, assist is proportional to the difference between the pressure representative signal 61 and the analog RMS value 62. Inspiratory assist is therefore provided only to compensate for the degree of incapacity of the patient. The patient still contributes to inspiration as a function of his capacity to prevent the lung ventilator to further reduce the patient's inability to breathe. Requiring breathing efforts from the patient usually accelerates recovery of the patient and faster disconnection of the patient from the lung ventilator.

Although the present invention has been described hereinabove with reference to preferred embodiments thereof, these embodiments can be modified at will, within the scope of the appended claims, without departing from the spirit and nature of the subject invention.

What is claimed is:

1. A method of controlling a lung ventilator in view of assisting inspiration of a patient, said lung ventilator comprising an inspiratory implement to be worn by the patient, an air supply system for supplying air to the inspiratory implement in order to assist patient's inspiration, and a control unit for controlling the air supply system in relation to an input signal, said method comprising the steps of:

detecting electromyographic signals produced by the patient's diaphragm by means of an array of electrodes passing through the center of the patient's diaphragm depolarizing region, each electrode-detected electromyographic signal comprising an electromyographic component and a noise component;

determining the position of the center of the patient's diaphragm depolarizing region by detecting a reversal of polarity of the electromyographic component of the electrode-detected electromyographic signals;

subtracting a first electromyographic signal detected by the electrodes of the array on a first side of the center of the patient's diaphragm depolarizing region, from a second electromyographic signal detected by the electrodes of the array on a second side, opposite to said first side, of the center of the patient's diaphragm depolarizing region, wherein (a) the first electrode-detected electromyographic signal has an electromyographic component of a first polarity, (b) the second electrode-detected electromyographic signal has an electromyographic component of a second polarity opposite to said first polarity, (c) the subtraction subtracts the noise components of the first and second electrode-detected electromyographic signals from each other but adds the respective electromyographic components of said first and second electrode-detected electromyographic signals together to produce an electromyographic signal of improved signal-to-noise ratio representative of a demand to inspire from the patient's brain; and supplying said electromyographic signal of improved signal-to-noise ratio as input signal to the control unit of the lung ventilator for controlling the air supply system and therefore the inspiration assist in relation to the electromyographic signal of improved signal-to-noise ratio.

2. A method of controlling a lung ventilator as recited in claim 1, wherein:

said array of electrodes is a linear array of electrodes and defines a plurality of pairs of successive electrodes;

the center of the patient's diaphragm depolarizing region is located between the electrodes of a given one of said pairs of successive electrodes;

said first electromyographic signal is detected through the pair of successive electrodes adjacent to said given pair on one side of said given pair; and said second electromyographic signal is detected through the pair of successive electrodes adjacent to said given pair on the other side of said given pair.

3. A method of controlling a lung ventilator as recited in claim 1, wherein said center position determining step comprises conducting a cross-correlation on the electrode-detected electromyographic signals.

4. A method of controlling a lung ventilator as recited in claim 3, wherein said center position determining step comprises removing a slow trend from the electrode-detected electromyographic signals prior to conducting said cross-correlation.

5. A method of controlling a lung ventilator as recited in claim 1, wherein said subtracting step is a time domain subtracting step.

6. A method of controlling a lung ventilator as recited in claim 1, wherein said subtracting step comprises the step of converting said first and second electromyographic signals in the frequency domain before carrying out said substraction.

7. A method of controlling a lung ventilator as recited in claim 1, wherein said electromyographic signal supplying step comprises:
   calculating an RMS value of the electromyographic signal of improved signal-to-noise ratio; and
   supplying said RMS value as input signal to the control unit of the lung ventilator.

8. A method of controlling a lung ventilator as recited in claim 1, wherein:
   said electromyographic signal detecting step comprises:
      analog-to-digital converting the electrode-detected electromyographic signals; and
   said electromyographic signal supplying step comprises:
      calculating a RMS value of the electromyographic signal of improved signal-to-noise ratio;
      digital-to-analog converting said RMS value; and
      supplying the analog RMS value as input signal to the control unit of the lung ventilator.

9. A method of controlling a lung ventilator as recited in claim 1, further comprising, prior to said subtracting step, the step of filtering from the electrode-detected electromyographic signals (I) motion artifacts, (ii) an ECG component and (iii) a disturbance from electrical mains.

10. A method of controlling a lung ventilator as recited in claim 1, further comprising the steps of:
   detecting the patient's respiratory pressure and producing a pressure representative signal;
   supplying the pressure representative signal to the control unit of the lung ventilator; and
   controlling, by means of the control unit, the air supply system in relation to a difference between said pressure representative signal and said electromyographic signal of improved signal-to-noise ratio.

11. A device for controlling a lung ventilator in view of assisting inspiration of a patient, said lung ventilator comprising an inspiratory implement to be worn by the patient, an air supply system for supplying air to the inspiratory implement in order to assist patient's inspiration, and a control unit for controlling the air supply system in relation to an input signal, said device comprising:
   an array of electrodes for detecting electromyographic signals produced by the patient's diaphragm, said array of electrodes passing through the center of the patient's diaphragm depolarizing region, and each electrode-detected electromyographic signal comprising an electromyographic component and a noise component;
   means for determining the position of the center of the patient's diaphragm depolarizing region by detecting a reversal of polarity of the electromyographic component of the electrode-detected electromyographic signals;
   means for subtracting a first electromyographic signal detected by the electrodes of the array on a first side of the center of the patient's diaphragm depolarizing region, from a second electromyographic signal detected by the electrodes of the array on a second side, opposite to said first side, of the center of the patient's diaphragm depolarizing region, wherein (a) the first electrode-detected electromyographic signal has an electromyographic component of a first polarity, (b) the second electrode-detected electromyographic signal has an electromyographic component of a second polarity opposite to said first polarity, (c) the subtraction subtracts the noise components of the first and second electrode-detected electromyographic signals from each other but adds the respective electromyographic components of said first and second electrode-detected electromyographic signals together to produce an electromyographic signal of improved signal-to-noise ratio representative of a demand to inspire from the patient's brain; and
   means for supplying said electromyographic signal of improved signal-to-noise ratio as input signal to the control unit of the lung ventilator for controlling the air supply system and therefore the inspiration assist in relation to the electromyographic signal of improved signal-to-noise ratio.

12. A device for controlling a lung ventilator as recited in claim 11, wherein:
   said array of electrodes is a linear array of electrodes and defines a plurality of pairs of successive electrodes;
   the center of the patient's diaphragm depolarizing region is located between the electrodes of a given one of said pairs of successive electrodes;
   said first electromyographic signal is detected through the pair of successive electrodes adjacent to said given pair on one side of said given pair; and
   said second electromyographic signal is detected through the pair of successive electrodes adjacent to said given pair on the other side of said given pair.

13. A device for controlling a lung ventilator as recited in claim 11, wherein said center position determining means comprises means for cross-correlating the electrode-detected electromyographic signals.

14. A device for controlling a lung ventilator as recited in claim 13, wherein said center position determining means comprises means for removing a slow trend from the electrode-detected electromyographic signals prior to cross-correlating the electrode-detected electromyographic signals.

15. A device for controlling a lung ventilator as recited in claim 11, wherein said subtracting means is a time domain subtracting means.

16. A device for controlling a lung ventilator as recited in claim 11, wherein said subtracting means comprises means for converting said first and second electrode-detected electromyographic signals in the frequency domain before carrying out said substraction.

17. A device for controlling a lung ventilator as recited in claim 11, wherein said electromyographic signal supplying means comprises:
   means for calculating a RMS value of the electromyographic signal of improved signal-to-noise ratio; and
   means for supplying said RMS value as input signal to the control unit of the lung ventilator.

18. A device for controlling a lung ventilator as recited in claim 11, further comprising means for analog-to-digital converting the electrode-detected electromyographic signals, wherein said electromyographic signal supplying means comprises:
   means for calculating a RMS value of the electromyographic signal of improved signal-to-noise ratio;

means for digital-to-analog converting said RMS value; and means for supplying the analog RMS value as input signal to the control unit of the lung ventilator.

19. A device for controlling a lung ventilator as recited in claim 11, further comprising means for filtering from the electrode-detected electromyographic signals (I) motion artifacts, (ii) an ECG component, and (iii) a disturbance from electrical mains, prior to said subtraction of the first electrode-detected electromyographic signal from the second electrode-detected electromyographic signal.

20. A device for controlling a lung ventilator as recited in claim 11, further comprising:

means for detecting the patient's respiratory pressure and for producing a pressure representative signal;

means for supplying the pressure representative signal to the control unit of the lung ventilator; and said control unit for controlling the air supply system in relation to a difference between said pressure representative signal and said electromyographic signal of improved signal-to-noise ratio.

21. A device for controlling a lung ventilator as recited in claim 11, wherein said array of electrodes is a linear array of electrodes mounted on a free end section of a catheter.

* * * * *